(12) United States Patent
Wen et al.

(10) Patent No.: US 11,644,189 B2
(45) Date of Patent: May 9, 2023

(54) MULTIFUNCTIONAL LED LAMP

(71) Applicants: Shanghai Sansi Electronic Engineering Co. Ltd., Shanghai (CN); Shanghai Sansi Technology Co. Ltd., Shanghai (CN); Jiashan Sansi Optoelectronic Technology Co. Ltd., Jiaxing (CN); Pujiang Sansi Optoelectronic Technology Co. Ltd., Jinhua (CN)

(72) Inventors: Xing Wen, Shanghai (CN); Shan Li, Shanghai (CN); Xiaobai Li, Shanghai (CN); Yongchao Xing, Shanghai (CN); Xiaoyong Wang, Shanghai (CN)

(73) Assignees: Shanghai Sansi Electronic Engineering Co. Ltd., Shanghai (CN); Shanghai Sansi Technology Co. Ltd., Shanghai (CN); Jiashan Sansi Optoelectronic Technology Co. Ltd., Zhejiang (CN); Pujiang Sansi Optoelectronic Technology Co. Ltd., Jinhua (CN)

( * ) Notice: Subject to any disclaimer, the term of this patent is extended or adjusted under 35 U.S.C. 154(b) by 0 days.

(21) Appl. No.: 17/353,828

(22) Filed: Jun. 22, 2021

(65) Prior Publication Data
US 2022/0074581 A1   Mar. 10, 2022

(30) Foreign Application Priority Data

Sep. 10, 2020 (CN) .......................... 202021978533.4

(51) Int. Cl.
*F21V 23/00* (2015.01)
*F21V 29/70* (2015.01)
(Continued)

(52) U.S. Cl.
CPC ............ *F21V 23/008* (2013.01); *F21V 29/70* (2015.01); *F21V 29/86* (2015.01); *G01P 13/00* (2013.01);
(Continued)

(58) Field of Classification Search
CPC ....... G01P 13/00; G06V 40/172; H04R 1/028; H04R 2420/07; F21V 23/008; F21V 29/70; F21V 29/86
See application file for complete search history.

(56) References Cited

U.S. PATENT DOCUMENTS 9,819,910 B2 * 11/2017 Huang ................. H05B 47/125
9,860,954 B1 *  1/2018 You ........................ H05B 45/10
(Continued)

*Primary Examiner* — Arman B Fallahkhair

(57) ABSTRACT

The present disclosure provides a multifunctional LED lamp, which includes: a main lamp body; one or more LED light-emitting modules connected with the main lamp body; a face recognition module disposed on the main lamp body; an infrared sensing module disposed on the main lamp body; a photosensitive module disposed on the main lamp body; and a control module in communication connection with the face recognition module, the infrared sensing module, and the photosensitive module. The multifunctional LED lamp includes multiple working modes, and the control module controls working states of the face recognition module, the infrared sensing module, and the photosensitive module to switch the working modes. By installing different sensors, the LED lamp of the present disclosure integrates various functions such as lighting, security warning, entertainment, lighting, health, etc., and can realize different working modes by combining different sensors.

8 Claims, 2 Drawing Sheets

(51) Int. Cl.
  *F21V 29/85*   (2015.01)
  *G06V 40/16*   (2022.01)
  *G01P 13/00*   (2006.01)
  *H04R 1/02*    (2006.01)
  *F21Y 105/18*  (2016.01)
  *F21Y 113/17*  (2016.01)
  *F21Y 115/10*  (2016.01)

(52) U.S. Cl.
  CPC ........... *G06V 40/172* (2022.01); *H04R 1/028* (2013.01); *F21Y 2105/18* (2016.08); *F21Y 2113/17* (2016.08); *F21Y 2115/10* (2016.08); *H04R 2420/07* (2013.01)

(56) References Cited

U.S. PATENT DOCUMENTS

| | | | |
|---|---|---|---|
| 9,955,551 B2* | 4/2018 | Spero | F21K 9/23 |
| 10,230,880 B2* | 3/2019 | Chien | F21V 21/30 |
| 10,389,982 B1* | 8/2019 | Fu | H04N 7/185 |
| 10,401,007 B1* | 9/2019 | York | H05B 47/19 |
| 11,297,772 B2* | 4/2022 | Hanson | A01G 7/045 |
| 11,297,775 B1* | 4/2022 | Quazi | F21V 23/005 |
| 2015/0116997 A1* | 4/2015 | Tappert | A01G 9/249 |
| | | | 362/249.03 |
| 2019/0072266 A1* | 3/2019 | Pollack | F21V 29/76 |
| 2019/0098725 A1* | 3/2019 | Sadwick | F21S 2/00 |
| 2019/0098842 A1* | 4/2019 | Barber, III | A01G 9/246 |
| 2019/0295207 A1* | 9/2019 | Day | G08B 21/02 |
| 2019/0368213 A1* | 12/2019 | Goldman | E04H 4/148 |
| 2021/0369905 A1* | 12/2021 | Bosua | H05B 47/17 |

* cited by examiner

MULTIFUNCTIONAL LED LAMP

CROSS REFERENCE TO RELATED APPLICATION

The present application claims the benefit of priority to Chinese Patent Application No. 2020219785334, entitled "Multifunctional LED Lamp", filed with CNIPA on Sep. 10, 2020, the content of which is incorporated herein by reference in its entirety.

FIELD OF DISCLOSURE

The present disclosure relates to the technical field of LED lamps, in particular, to a multifunctional LED lamp.

BACKGROUND

With the continuous improvement of people's living standards, people have more and more requirements for lights. Lamps are no longer lighting in a simple sense. Lamps are also expected to realize other functions such as security warning, entertainment and leisure, lighting, health and so on. With the increase in these demands, there are now more and more types of lamps. However, if each lamp has only one additional function in addition to lighting, each time a function is required, it is necessary to purchase a lamp with a corresponding function, which not only makes the purchased lamps have repeated lighting functions, but also greatly increases the cost of installation, procurement, electricity and other costs, which even exceeds the value of the lamps themselves. Therefore, there is an urgent need in this field for a lamp that integrates multiple functions.

SUMMARY

The present disclosure provides a multifunctional LED lamp, which includes: a main lamp body; one or more LED light-emitting modules connected with the main lamp body; a face recognition module disposed on the main lamp body; an infrared sensing module disposed on the main lamp body; a photosensitive module disposed on the main lamp body; and a control module disposed on the main lamp body and is in communication connection with the face recognition module, the infrared sensing module, and the photosensitive module, wherein the control module controls working states of the face recognition module, the infrared sensing module, and the photosensitive module to switch the multifunctional LED lamp in a plurality of working modes.

In some examples, the plurality of working modes includes a smart mode, a monitoring mode, or a night sensing mode; in the smart mode, the face recognition module, the infrared sensing module, and the photosensitive module are all set to a working state; in the monitoring mode, the face recognition module is set to the working state while the infrared sensing module and the photosensitive module are both set to a non-working state; in the night sensing mode, the infrared sensing module is set to the working state and the face recognition module and the photosensitive module are both set to the non-working state.

In some examples, the multifunctional LED lamp further includes a power drive module electrically connected with the control module, the LED light-emitting module, the face recognition module, the infrared sensing module, and the photosensitive module for power supply.

In some examples, the multifunctional LED lamp further includes a loudspeaker module connected with the control module to voice out a current working mode of the multifunctional LED lamp; wherein the loudspeaker module is disposed on the main lamp body or establishes a wireless communication connection with the main lamp body.

In some examples, the multifunctional LED lamp further includes an indicator module in communication connection with the control module to display a current working mode of the multifunctional LED light through a color and/or flashing frequency of an indicator.

In some examples, the multifunctional LED lamp further includes an Internet of Things module connected with the control module to establish a communication connection with an external device.

In some examples, the LED light-emitting module includes an LED light emitter, an LED heat sink, and an LED light distribution structure; wherein the LED heat sink is configured to dissipate heat of the LED light emitter, and the LED light distribution structure is configured to seal an optical cavity and perform secondary light distribution.

In some examples, the LED heat sink includes a ceramic heat sink, and the LED light emitter is attached to a surface of the ceramic heat sink.

In some examples, the LED light emitter includes LED chips of different colors.

In some examples, the LED light emitter at least includes an LED chip that emits UVA light.

As mentioned above, the multifunctional LED lamp of the present disclosure has the following beneficial effects: by installing different sensors, the LED lamp of the present disclosure integrates various functions such as lighting, security warning, entertainment, lighting, health, etc., and can realize different working modes by combining different sensors. The LED lamp is very flexible, and can satisfy the user to realize multiple functions in the case of buying a single lamp, thus the user experience is greatly improved.

DETAILED DESCRIPTION OF THE PREFERRED EMBODIMENTS

Figure 1:
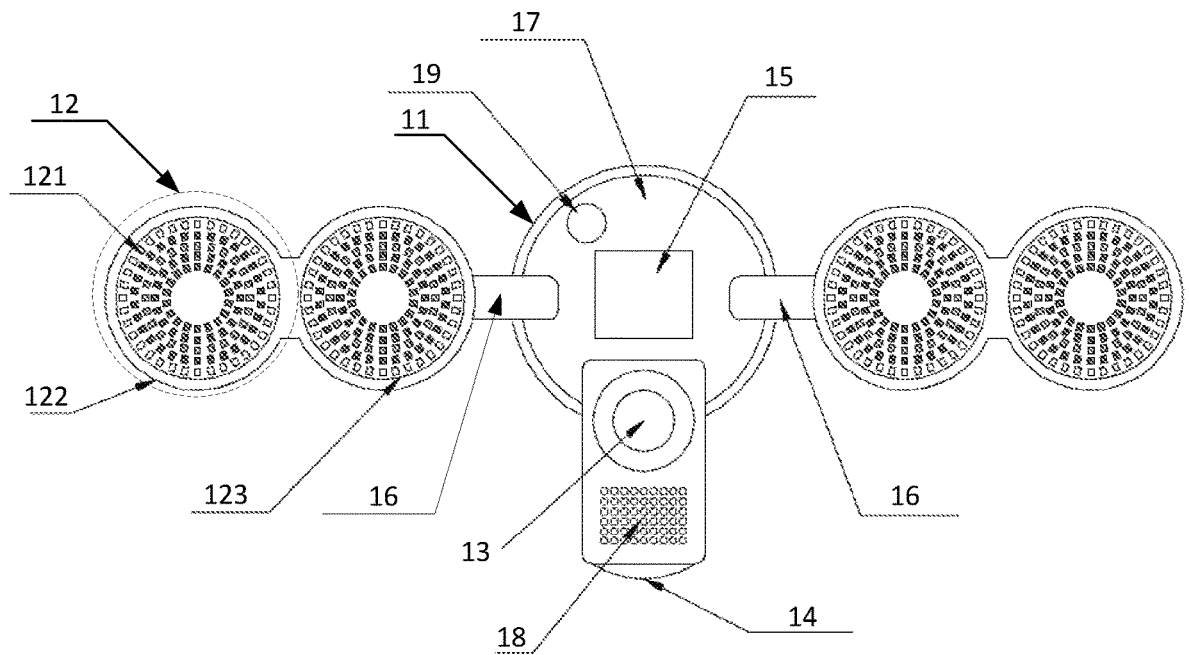
FIG. 1 shows a schematic view of a multifunctional LED lamp according to an embodiment of the present disclosure.

The embodiments of the present disclosure will be described below. Those skilled may easily understand other advantages and effects of the present disclosure according to contents disclosed by the specification.

It should be understood that the structures, proportions, sizes, and the like, which are illustrated in the drawings of the present specification, are only used to clarify the contents disclosed in the specification for understanding and reading by those skilled, and are not intended to limit the implementation of the present disclosure, thus are not technically meaningful. Any modification of the structure, change of the scale, or adjustment of the size should still fall within the scope of the technical contents disclosed by the present disclosure without affecting the effects and achievable objectives of the present disclosure. The following detailed description should not be considered limiting, and the scope of the embodiments of the present disclosure is limited only by the claims of the patents. The terms used herein are for describing particular embodiments only, and are not intended to limit the present disclosure. Spatially related terms, such as "upper", "lower", "left", "right", "downward", "below", "bottom", "above", "top", etc., can be used in the text for ease of explanation of the relationship between one element or feature and another element or feature shown in the figure.

In the present disclosure, unless otherwise clearly specified and limited, the terms "install", "connect", "couple", "fix", "hold" and other terms should be understood in a broad sense. For example, it can be a fixed connection, a detachable connection, or an integral connection. It can be a mechanical connection or an electrical connection. It can be a direct connection, or indirect connection through an intermediate medium, or it can be an internal communication between two components. Those of ordinary skill in the art can understand the specific meanings of the above terms in the present disclosure according to specific situations.

In addition, as used herein, the singular forms "a", "an" and "the" are intended to include the plural forms as well, unless the context clearly indicates otherwise. It should be further understood that the terms "comprise", "include" indicate that there are the described features, operations, elements, components, items, categories, and/or groups, but the existence, appearance, or addition of one or more other features, operations, elements, components, items, categories, and/or groups are not excluded. The terms "or" and "and/or" are used herein to be interpreted as inclusive or meaning any one or any combination. Therefore, "A, B or C" or "A, B and/or C" means "any of the following: A; B; C; A and B; A and C; B and C; A, B and C". An exception to this definition occurs only when a combination of elements, functions, or operations are inherently mutually exclusive in some manner.

Since the traditional lamps usually have only one function, they cannot integrate multiple functions such as security warning, entertainment and leisure, lighting, health, etc., which leads users to purchase a lamp every time they need a function. This not only repeats the lighting function, but also greatly increases the cost of installation, purchase, and electricity. The cost even exceeds the value of the lamp itself. In view of this, the present disclosure provides a multifunctional intelligent lamp. Through the integration of different sensors, the lamp has multiple functions such as lighting, security warning, entertainment, illuminating, and health. The lamp can also use the face recognition module for face recognition, and can correspondingly emit lights of different colors to achieve the purpose of warning.

In order to make the purpose, technical solutions and advantages of the present disclosure clearer, the technical solutions in the embodiments of the present disclosure will be further described in detail through the following embodiments and the accompanying drawings. It should be understood that the specific embodiments described here are only used to explain the present disclosure, but not used to limit the present disclosure.

FIG. 1 shows a schematic view of a multifunctional LED lamp according to an embodiment of the present disclosure. The multifunctional LED lamp of this embodiment includes a main lamp body 11, at least one or more LED light-emitting modules 12, a face recognition module 13, an infrared sensing module 14, a photosensitive module (not shown), and a control module 15. The LED light-emitting module 12 is connected with the main light body 11 through a connection structure 16. The face recognition module 13, the infrared sensing module 14, and the photosensitive module are all disposed on the main light body 11. The control module 15 is in communication connection with the face identification module 13, the infrared sensing module 14, and the photosensitive module. The multifunctional LED lamp includes multiple working modes, and the control module controls working states of the face recognition module 13, the infrared sensing module 14, and the photosensitive module to switch the working modes.

In this embodiment, the multifunctional LED lamp further includes a power drive module (not shown) electrically connected with the control module 15, the LED light-emitting module 12, the face recognition module 13, the infrared sensing module 14, and the photosensitive module for power supply. The power drive module is installed in the power supply cavity of the main lamp body, and the modules can be connected with each other by wires or connectors to achieve electrical communication.

Specifically, the face recognition module 13 includes a camera for performing face recognition, collects a user's face image and recognizes the face image. The infrared sensing module 14 includes a human body infrared motion sensor, which is used to detect the motion of the human body. The photosensitive module includes a photosensitive sensor, which is a sensitive device that has a response or conversion function to external light signals or light radiation, and can be used to sense day and night. The power drive module supplies power to the power consumption modules in the lamp. Specifically, the power drive module may be a switching constant current source circuit, a linear IC power supply circuit, or a resistance-capacitance step-down power supply circuit, etc. The control module 15 is installed in the drive housing 17, which may be an Advanced RISC Machines (ARM) controller, a Field Programmable Gate Array (FPGA) controller, a System on Chip (SoC) controller, a Digital Signal Processing (DSP) controller, or a Microcontroller Unit (MCU) controller, etc.

In this embodiment, the multifunctional LED lamp includes multiple working modes, and the working states of the face recognition module 13, the infrared sensing module 14, and the photosensitive module are adjusted to switch the working modes. The working mode includes, for example, a smart mode for all modules, a monitoring mode and a night sensing mode for some modules. The multifunctional LED lamp may flexibly set the working status of the face recognition module 13, the infrared sensing module 14, and the photosensitive module. The combination of different modules may form different working modes. For example, if the face recognition module 13, the infrared sensing module 14, and the photosensitive module are set to the working state at the same time, then the multifunctional LED lamp will work in the smart mode. Only the face recognition module 13 is set to the working state, and the infrared sensing module 14 and the photosensitive module are set to the non-working state, then the multifunctional LED lamp works in the monitoring mode. Only the infrared sensing module 14 is set to the working state, and the face recognition module 13 and the photosensitive module are set to the non-working state, then the multifunctional LED lamp works in the night sensing mode. Therefore, the multifunctional LED provided in this embodiment adopts multiple working modes, which may flexibly adapt to the needs of different users and effectively reduce power consumption.

In some examples, the multifunctional LED lamp further includes a loudspeaker module 18, which broadcasts the current working mode of the LED lamp in the form of voice, such as smart mode, monitoring mode, or night sensing mode, etc., so that the users are informed the current working mode of the lamp in time and conveniently. The multifunctional LED lamp may include multiple loudspeaker modules 18, which may be directly installed on the main lamp body 11, or may establish a wireless communication connection with the main lamp body 11, so that they may work separated from the main lamp body 11 and may be placed in any desired position, which is more flexible. In addition, the parameter setting and playback content of the loudspeaker module 18 may be customized by the users according to the actual situation.

In some examples, the multifunctional LED lamp further includes an indicator module 19 to notify the current working mode of the LED lamp through the color of the indicator. For example, a red indicator indicates that the LED lamp is currently working in the smart mode, a blue indicator indicates that the LED lamp is currently working in the monitoring mode, and a yellow indicator indicates that the LED lamp is currently working in the night sensing mode.

In some examples, the multifunctional LED lamp further includes an Internet of Things module (not shown) to connect the LED lamp to the Internet, so that the lamp data may be uploaded to the Internet or downloaded from the Internet. The Internet of Things module includes but is not limited to Bluetooth module, ZigBee module, NB-IoT module, Wi-FI module, etc. In some preferred implementations, the Internet of Things module is connected to the mobile phone APP, and the multifunctional LED lamp may send the lamp data to the mobile phone APP through the Internet of Things module. The lamp data may be displayed in the page of the mobile phone APP, and the users may send light control commands to the LED lamp through the mobile phone APP.

The multifunctional LED lamp of the present disclosure is a hardware device. The LED light-emitting module 12, the face recognition module 13, the infrared sensing module 14, the photosensitive module (not shown), the power drive module (not shown), and the control module 15 inside the multifunctional LED lamp are all hardware modules, and the present disclosure only relates to and protects the hardware functions. The LED lamp of the present disclosure may be used alone, or may be used in combination with some traditional software or programs, such as the combination of the aforementioned content with the mobile phone APP for data interaction, etc. However, the present disclosure does not involve anything about the updates of the software technology.

In some examples, the control module 15 is connected with the face recognition module 13, the loudspeaker module 18, and the indicator module 19, respectively. The face recognition module 13 obtains the physical features of the current user and recognizes the identity of the user. If the similarity between the physical features of the current user and the preset physical features is higher than the preset threshold, it can be considered that the current user is not a stranger (such as the user, a relative of the user, etc.), otherwise the current user is considered to be a stranger, and the face recognition module 13 will send the identification result to the control module 15.

After receiving the identity recognition result, the control module 15 may perform the following operations in combination with some software or programs: the control module 15 controls the indicator module 19 and the loudspeaker module 18 to perform corresponding tasks according to the face recognition result. For example, if the face recognition result is that the current user is a stranger, the indicator module 19 is controlled to emit a red light and flashing, and the loudspeaker module 18 is controlled to emit a warning sound. If the face recognition result is that the current user is not a stranger but the owner of the house, the indicator module 19 is controlled to emit a white light normally used for lighting and keep the light on for a period of time (the length of time may be set through the mobile APP). If the face recognition result is that the current user is not the owner of the house but the relative of the owner of the house, the indicator module 19 is controlled to emit a warm white light, and a welcome speech is played through the loudspeaker module 18.

In some examples, the LED light-emitting module 12 includes an LED light emitter 121, an LED heat sink 122, and an LED light distribution structure 123, which are indicated by a dotted circle in the figure for ease of understanding. The LED heat sink 122 dissipates the heat of the LED light emitter 121, and the LED light distribution structure 123 seals an optical cavity and performs secondary light distribution. The LED light-emitting module includes one or more independently controllable LED light emitters, and these LED light emitters are allowed to be controlled individually or may be set to be controlled at the same time.

Figure 2A:
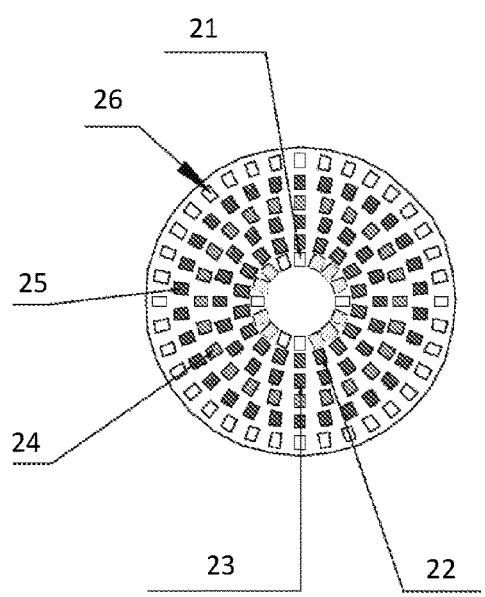
FIG. 2A shows a schematic view of an LED light emitter according to an embodiment of the present disclosure.
Figure 2B:
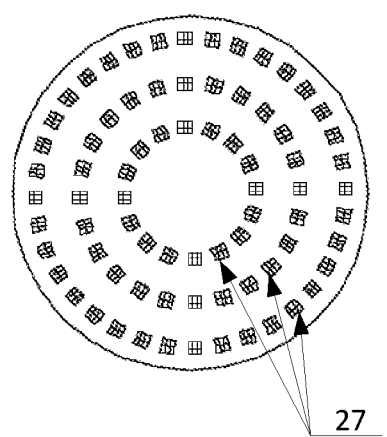
FIG. 2B shows a schematic view of an LED light emitter according to an embodiment of the present disclosure.

Optionally, the LED light emitter 121 may include monochromatic LED chips, or may include integrated LED chips. FIG. 2A shows the LED light emitter including the monochromatic LED chips. From the inside to the outside of the LED light emitter, warm white LED chips 21 are disposed on the first circle, UVA LED chips are disposed on the second circle, and blue LED chips 23 are disposed on the third circle, green LED chips 24 are disposed on the fourth circle, red LED chips 25 are disposed on the fifth circle, and cool white LED chips 26 are disposed on the sixth circle (i.e. the outermost circle). FIG. 2B shows the LED light emitter including integrated LED chips, the integrated LED chips 27 are disposed on each circle from the inside to the outside of the LED light emitter.

In some examples, the LED light emitter at least includes an LED chip that emits UVA light. The LED lamp may be set to emit only UVA light to sterilize and remove mites from the illuminated area. When the infrared sensing module 14 senses that someone enters the irradiation range, the LED lamp will automatically turn off to prevent long-term exposure to UVA light which may cause harm to the human body. When it is confirmed that there are no people or animals in the irradiation area (i.e., the infrared sensing module 14 does not sense anyone), the LED lamp will automatically start again.

In some examples, the LED heat sink is made of a ceramic material with excellent heat dissipation performance. The LED light-emitting module is usually attached to an aluminum substrate and the heat is dissipated by the LED heat sink. However, if the material of the heat sink is ceramic, the LED light emitter may be directly attached to the surface of the ceramic heat sink. The LED light distribution structure in this embodiment is an optical device that may be used for optical cavity sealing and may perform secondary light distribution, such as LENS, DIFFUSER, and the like.

In some examples, the LED light emitter includes LED chips of different colors. These LED chips of different colors may adapt to different lighting environments and create different space effects. For example, red and orange give people a warm feeling. Blue and purple give people a cold feeling. In addition, when adjusting the atmosphere by using the lighting, the lamps may be set to the color gradient, color jump and other modes through the mobile phone APP to effectively adjust the atmosphere.

The multifunctional LED lamp of the present disclosure is a hardware device, and the modules included in the lamp are also hardware modules. The multifunctional LED lamp may be used in combination with software or programs, but the present disclosure does not involve any updates of the software technology.

In summary, the present disclosure provides a multifunctional LED lamp, by installing different sensors, the LED lamp integrates various functions such as lighting, security warning, entertainment, lighting, health, etc., and can realize different working modes by combining different sensors. The LED lamp is very flexible, and can satisfy the user to realize multiple functions in the case of buying a single lamp, thus the user experience is greatly improved. Therefore, the present disclosure effectively overcomes various shortcomings in the existing technology and has high industrial utilization value.

The above-mentioned embodiments are just used for exemplarily describing the principle and effects of the present disclosure instead of limiting the present disclosure. Those skilled in the art can make modifications or changes to the above-mentioned embodiments without going against the spirit and the range of the present disclosure. Therefore, all equivalent modifications or changes made by those who have common knowledge in the art without departing from the spirit and technical concept disclosed by the present disclosure shall be still covered by the claims of the present disclosure.

The invention claimed is:

1. A multifunctional LED lamp, comprising:
a main lamp body;
one or more LED light-emitting modules connected with the main lamp body;
a face recognition module disposed on the main lamp body;
an infrared sensing module disposed on the main lamp body;
a photosensitive module disposed on the main lamp body; and
a control module disposed on the main lamp body and is in communication connection with the face recognition module, the infrared sensing module, and the photosensitive module, wherein
the control module controls working states of the face recognition module, the infrared sensing module, and the photosensitive module to switch the multifunctional LED lamp in a plurality of working modes; and
the LED light-emitting module comprises an LED light emitter, the LED light emitter comprises a plurality of LED chips, wherein the plurality of LED chips comprises warm white LED chips, blue LED chips and UVA LED chips, wherein the UVA LED chips emit UVA light and are disposed between the warm white LED chips and the blue LED chips;
wherein the LED light emitter comprises the plurality of LED chips distributed in rows of concentric circles including, from a center to an outermost circle of the arrays, the warm white LED chips, the UVA LED chips, the blue LED chips, green LED chips, red LED chips and cool white LED chips.

2. The multifunctional LED lamp according to claim 1, wherein the LED light-emitting module further comprises:
an LED heat sink configured to dissipate heat of the LED light emitter; and
an LED light distribution structure configured to seal an optical cavity and perform secondary light distribution.

3. The multifunctional LED lamp according to claim 2, wherein the LED heat sink comprises a ceramic heat sink, and the LED light emitter is attached to a surface of the ceramic heat sink.

4. The multifunctional LED lamp according to claim 1, wherein the plurality of working modes includes a smart mode, a monitoring mode, or a night sensing mode, wherein
in the smart mode, the face recognition module, the infrared sensing module, and the photosensitive module are all set to a working state;
in the monitoring mode, the face recognition module is set to the working state while the infrared sensing module and the photosensitive module are both set to a non-working state; and
in the night sensing mode, the infrared sensing module is set to the working state and the face recognition module and the photosensitive module are both set to the non-working state.

5. The multifunctional LED lamp according to claim 1, further comprising:
a power drive module electrically connected with the control module, the LED light-emitting module, the face recognition module, the infrared sensing module, and the photosensitive module for power supply.

6. The multifunctional LED lamp according to claim 1, further comprising:
a loudspeaker module connected with the control module to voice out a current working mode of the multifunctional LED lamp; wherein the loudspeaker module establishes a wireless communication connection with the main lamp body.

7. The multifunctional LED lamp according to claim 1, further comprising:
an indicator module in communication connection with the control module to display a current working mode of the multifunctional LED light through a color and/or flashing frequency of an indicator.

8. The multifunctional LED lamp according to claim 1, wherein the control module is installed in a drive housing, and is an Advanced RISC Machines controller, a Field Programmable Gate Array controller, a System on Chip controller, a Digital Signal Processing controller, or a Micorcontroller Unit (MCU) controller.

* * * * *